United States Patent
Adams, Jr. et al.

(10) Patent No.: US 8,381,410 B2
(45) Date of Patent: Feb. 26, 2013

(54) BREAST IMPLANT SELECTOR SYSTEMS

(75) Inventors: William P. Adams, Jr., University Park, TX (US); Bradley P. Bengston, Grand Rapids, MI (US); Steven A. Teitelbaum, Los Angeles, CA (US)

(73) Assignee: Allergan, Inc., Irvine, CA (US)

( * ) Notice: Subject to any disclaimer, the term of this patent is extended or adjusted under 35 U.S.C. 154(b) by 1 day.

(21) Appl. No.: 13/155,619

(22) Filed: Jun. 8, 2011

(65) Prior Publication Data

US 2011/0238175 A1 Sep. 29, 2011

Related U.S. Application Data

(63) Continuation of application No. 12/707,837, filed on Feb. 18, 2010, now Pat. No. 7,979,996, which is a continuation of application No. 12/217,984, filed on Jul. 10, 2008, now Pat. No. 7,685,721.

(60) Provisional application No. 60/961,161, filed on Jul. 19, 2007.

(51) Int. Cl.
*A61B 5/107* (2006.01)

(52) U.S. Cl. ........... 33/512; 33/1 SD; 600/587; 623/912

(58) Field of Classification Search .................. 33/1 SB, 33/1 SD, 511, 512; 235/85 R; 600/587; 623/912
See application file for complete search history.

(56) References Cited

U.S. PATENT DOCUMENTS

| | | | |
|---|---|---|---|
| 1,681,740 A | 8/1928 | Meyers | |
| 2,559,501 A | 7/1951 | Graf | |
| 4,024,856 A | 5/1977 | Kirianoff | |
| 4,189,634 A | 2/1980 | LaBove et al. | |
| 4,219,029 A | 8/1980 | Grossman et al. | |
| 4,338,953 A | 7/1982 | Ward | |
| 4,772,780 A | 9/1988 | Reed et al. | |
| 6,311,403 B1 | 11/2001 | Macrini | |
| 6,467,180 B1 | 10/2002 | Chan | |
| 6,981,988 B1 | 1/2006 | Kinsley | |
| 7,685,721 B2 | 3/2010 | Adams et al. | |
| 7,955,274 B2* | 6/2011 | Lalonde | 600/587 |
| 7,979,996 B2* | 7/2011 | Adams et al. | 33/512 |
| 2006/0136069 A1 | 6/2006 | Franca | |
| 2007/0203605 A1 | 8/2007 | Melton et al. | |
| 2008/0125675 A1 | 5/2008 | Lalonde | |
| 2009/0112130 A1 | 4/2009 | Bengtson | |
| 2009/0137894 A1 | 5/2009 | Olson | |
| 2009/0181104 A1 | 7/2009 | Rigotti et al. | |
| 2009/0198154 A1 | 8/2009 | Roshdieh et al. | |
| 2009/0227904 A1 | 9/2009 | Mordaunt et al. | |

(Continued)

FOREIGN PATENT DOCUMENTS

| | | |
|---|---|---|
| DE | 20306638 | 6/2003 |
| WO | 20100049926 | 5/2010 |

OTHER PUBLICATIONS

Tebbetts et al., "Five Critical Decisions in Breast Augmentation Using Five Measurements in 5 Minutes: The High Five Decision Support Process", The High Five System, vol. 116, No. 7, pp. 2005-2016, Oct. 2005.

(Continued)

*Primary Examiner* — G. Bradley Bennett
(74) *Attorney, Agent, or Firm* — Linda Fox; Stephen Donovan; Debra Condino

(57) ABSTRACT

A breast implant selector system including a breast width selector for selecting breast width input information, a breast tissue type selector for selecting breast tissue type input information in response to breast width input information selected with the breast width selector, and an implant size selector for selecting implant size input information in response to the breast tissue type input information selected with the breast tissue type selector. A result indicator provides a result characterizing at least one suggested breast implant as a function of the input breast width, breast tissue type, and implant size input information.

10 Claims, 3 Drawing Sheets

U.S. PATENT DOCUMENTS

2009/0287119 A1    11/2009   Chapman
2010/0081971 A1    4/2010   Allison
2012/0123244 A1*   5/2012   Hashimshony et al. ...... 600/587

OTHER PUBLICATIONS

Haines, "Women to "chest drive" Bulgarian airbags" The Register, Jan. 12, 2010, XP002668788, URL:http://www.theregister.co.uk/2010/01/12/biodynamics_analysis/print.html.

Anonymous, "Optimale Brust-OP mit BioDynamic Breast (CAIS)", Praxisklinik Dr. Bosselmann & Dr. Siepe, Jun. 26, 2007, XP002668789, URL:http://www.bosselmann-siepe.de/behandlung-bonn/plastische-chirurgie/brustvergroserung-bonn/biodynamic-breast-cais.html.

* cited by examiner

BREAST IMPLANT SELECTOR SYSTEMS

CROSS-REFERENCE TO RELATED APPLICATIONS

The present application is a continuation of U.S. patent application Ser. No. 12/707,837, filed Feb. 18, 2010, which is a continuation of U.S. patent application Ser. No. 12/217,984, filed Jul. 10, 2008, now U.S. Pat. No. 7,685,721, which claims the benefit of U.S. Provisional Patent Application No. 60/961,161, filed Jul. 19, 2007, the entire contents of each of which are incorporated herein by reference.

FIELD OF INVENTION

The present invention relates in general to plastic surgery techniques, and in particular breast implant selector systems suitable for selecting breast implants prior to breast augmentation surgery.

BACKGROUND OF INVENTION

Breast augmentation is one of the most common cosmetic surgical procedures performed in the United States and Europe. In 2006, almost 400,000 women in the United States chose breast implantation surgery to meet their personal goals. Breast augmentation is, for example, often chosen for enhancing figure proportions, for remedying breast droop or sag due to age, nursing, or weight loss, or for symmetry correction during breast reconstruction after cancer surgery. Studies have also shown that breast augmentation can lead to an improved quality of life. Whatever the reason chosen for breast augmentation, the choice of the appropriate breast implant is the first crucial step in the process of realizing the patient's goals.

Each woman who elects breast augmentation surgery not only has her own personal expectations, but also her own unique set of physical characteristics. Certainly the patient and the doctor must consider the patient's desired post-operative breast size and profile; however, the physical characteristics of the patient's breast, including tissue and skin characteristics, also must be carefully considered. In particular, the failure to clinically select a breast implant of the appropriate volume and shape can lead to disappointing aesthetic results, potentially uncorrectable deformities, or even the need for re-operation. Re-operation, which generally occurs with a frequency of ten to twenty percent (10-20%) after three (3) years, not only unnecessarily exposes the patient to additional surgery, but is also costly in terms of both the additional surgical procedure itself and the replacement implants.

Given the wide range of patient goals and differing physical characteristics, a relatively large range of breast implants have been developed and marketed. (Counting types, sizes, shapes, and so on, over two hundred [200] different implants are available in the United States alone.) While this wide range of choices advantageously allows patients and doctors the flexibility to choose the appropriate implant, the array of choices can also make the decision process more complicated, for both patient and doctor.

In other words, patients and their doctors need a better way of selecting the best possible breast implant from the relative large number of choices available in the marketplace. Any new breast implant selection techniques must not only address the aesthetic goals of the patient, but also the constraints imposed by the patient's physical characteristics. Such techniques should be accurate and minimize the risk of disappointing results and re-operation, yet still simply the selection process.

SUMMARY OF INVENTION

The principles of the present invention are embodied in breast implant selector systems that provide doctor and patient with the ability to easily and accurately select an appropriate breast implant in view of the patient's goals and physical characteristics. According to one particular exemplary embodiment, a breast implant selector system is disclosed that includes a breast width selector that allows for the input of breast width information, a breast tissue type selector that allows for the input of breast tissue type information, and an implant size selector allows for the input implant size information. A result indicator provides a result characterizing at least one suggested breast implant as a function of the input breast width, breast tissue type, and implant size information.

Embodiments of the present principles advantageously provide an easy to use system by which doctors and patients can select the best possible implant in view of the patient's goals and physical characteristics. In addition to being easy to use, these systems are accurate and minimize the risk of disappointing results and reoperation.

BRIEF DESCRIPTION OF DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
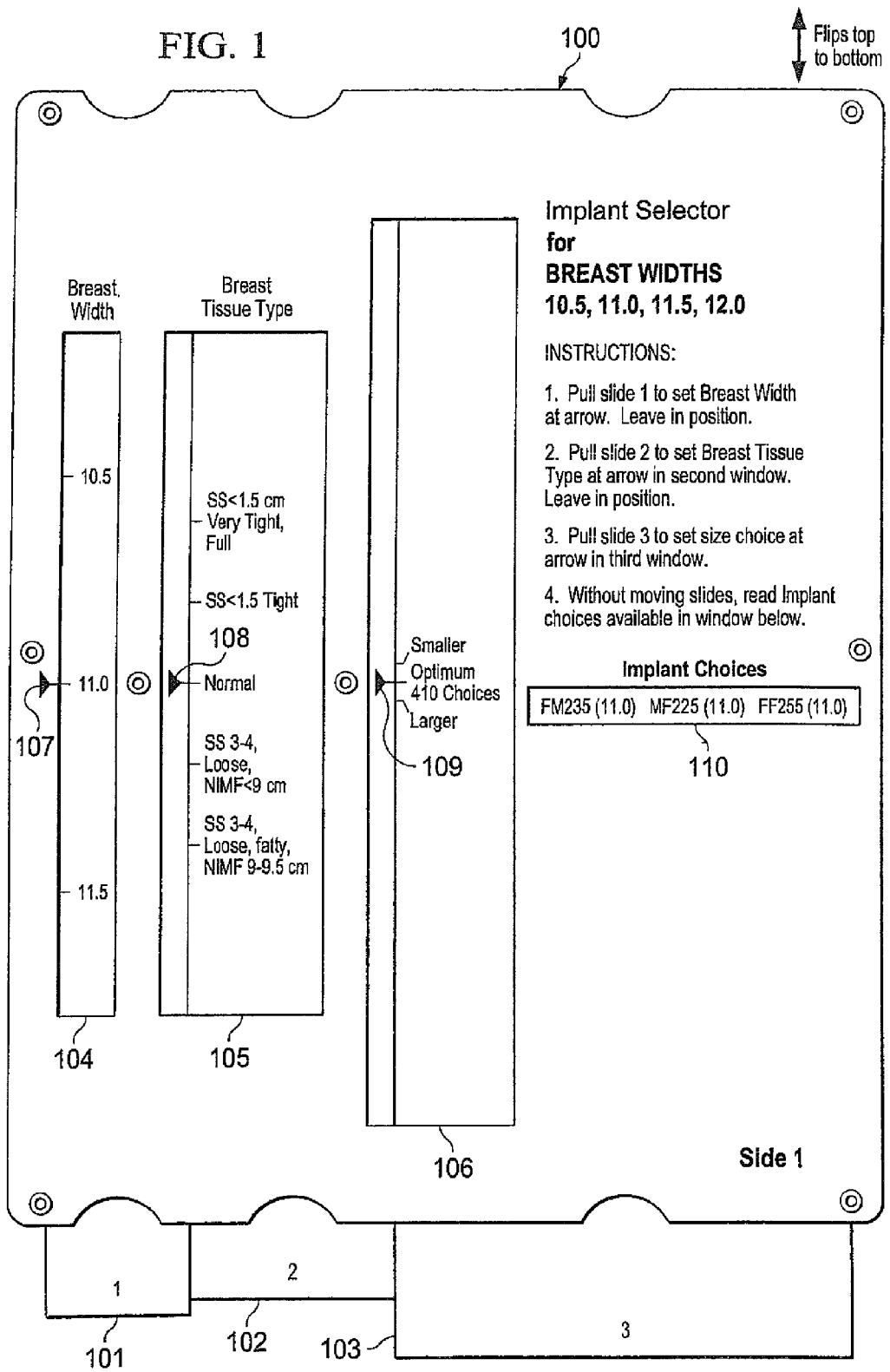
FIG. 1 is a diagram of a selected side of a first breast implant selector embodying the principles of the present invention.
Figure 2:
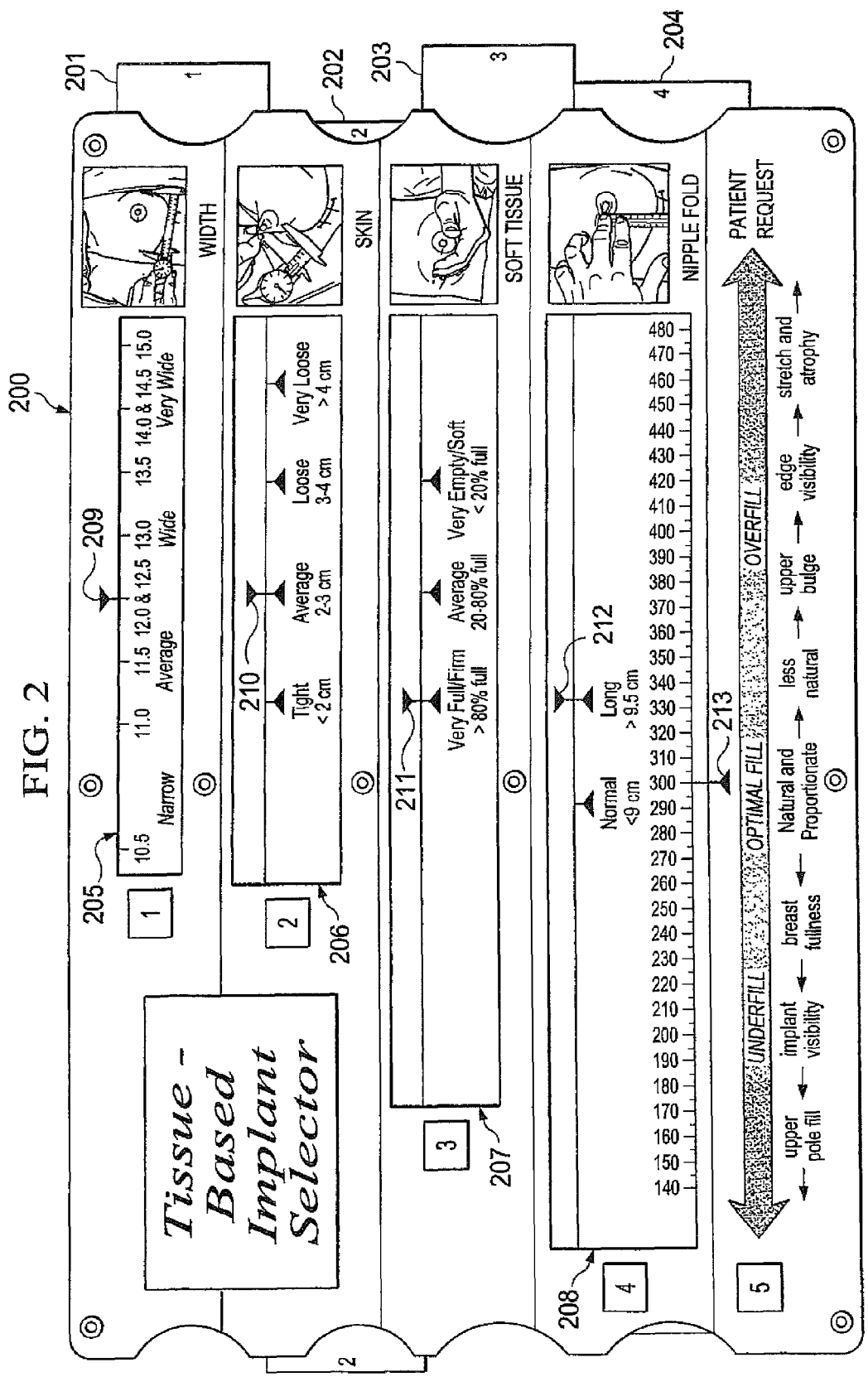
FIG. 2 is a diagram of a selected side of a second breast implant selector embodying the principles of the present invention.

The principles of the present invention and their advantages are best understood by referring to the illustrated embodiment depicted in FIGS. 1-2 of the drawings, in which like numbers designate like parts.

FIG. 1 is a diagram of one exemplary breast selector system 100 embodying the principles of the present invention. Breast selector 100 includes three (3) information-bearing movable slides (selectors) 101, 102, and 103 and three (3) corresponding windows 104, 105, and 106, which allow the information on movable slides 101-103 to be viewed during operation of breast selector 100. In the preferred embodiment of breast selector system 100, slides 101-103 and windows 104-106 implement a selection algorithm based on three (3) input criteria, namely, measured breast width, measured or observed breast tissue type, and a degree of freedom in implant size. In the illustrated embodiment, the result of applying the algorithm to the input criteria is the commercial designator of a suggested product available in the marketplace, although in alternate embodiments another form of result, for example implant fill, could be provided as the output result.

Breast width slide 101 of breast selector 100 bears a set of spaced apart marks or indicia that allow the doctor to input the measured breast width of the patient, in centimeters (cm), by aligning the corresponding breast width mark visible through breast width window 104 with fixed arrow 107 on the body of breast selector 100. In the illustrated embodiment, breast selector 100 has windows and slide markings on both sides, with the side visible in FIG. 1 corresponding to breast widths of 10.0 cm up to 12.0 cm, in increments of 0.5 cm, and the opposite (out-of-view) side corresponding to breast widths of 12.5 cm up to 14.0 cm, in increments of 0.5 cm. The alignment of the measured breast width mark on slide 101 with fixed arrow 107 in turn positions movable arrow 108, borne on the edge of breast width slide 101, within breast tissue type window 105.

Breast tissue slide 102 allows the doctor to align a mark associated with the patient's measured or observed breast tissue type with movable arrow 108, as set by breast width slide 101. In the illustrated embodiment, the five (5) different breast tissue type marks borne by breast tissue type slide 102 correspond to very tight/full, tight, normal, loose, and loose/fatty. (These five (5) breast tissue types are generally derived from skin stretch and nipple-to-fold measurements, along with subjective observations; in alternate embodiments, different breast tissue types (characterizations) may be used.) In turn, movable arrow 109, which is disposed on the edge of breast tissue type slide 102, moves a corresponding amount within breast size window 106.

Breast size window 106 and breast size slide 103 allow the patient and doctor to decide whether the implant will be the corresponding optimum choice from the set of available choices or will be smaller or larger than optimum. The recommended implant choices, which are provided on breast size slide 103, then appear in window 110. In the illustrated embodiment shown in FIG. 1, window 110 displays alternate choices within the Allergan 410 family of implants, in this case the FM235 (11.0), MF225 (11.0), and FF255 (11.0) implants. Generally, the Allergan 410 series of implants are form-stable, cohesive, anatomically shaped, and textured implants. The FM235 (11.0) implant has a volume of 235 cc, with full height and moderate projection and a width of 11.0 cm. The MF225 (11.0) implant has a volume of 225 cc, with moderate height and full projection and a width of 11.0 cm. The FF255 (11.0) implant has a volume of 255 cc, with full height and full projection and a width of 11.0 cm.

A more complete set of correlations between breast width, breast tissue type, breast implant size, and the Allergan 410 product family are provided in Tables 1-9. Generally, the information of Tables 1-9 is based on the substantial surgical experience of the inventors in using over one thousand (1000) Allergan 410 form stable implants, clinical observation, and heuristics, in view of the physical characteristics of the implants themselves.

Additionally, each designator number shown in window 110 of breast selector system 100 may be associated with a corresponding post-operative nipple-to fold length value, for example in another color or font. Advantageously, the provided nipple-to-fold length value, will assist the surgeon in properly placing the incision during surgery.

Application of the principles of the present invention are not limited to the breast implant choices made available by any given manufacturer or any particular type or shape of implant. Moreover, the types, sizes, and shapes of the breast implants available in the marketplace may change as the manufacture develop new products. In particular, the inventive principles can be applied to many different types of implants, including silicone gel and saline, form-stable and non-form stable, anatomic shaped and round, textured or smooth, as well as of different heights and projections. For example, Tables 10-18 contain exemplary data characterizing the Allergan 10-15-20 smooth, round, gel implants and suitable for use in an alternate embodiment of selector 100.

Advantageously, breast implant selector 100 allows the doctor and patient to select an implant that best meets the patient's goals, while avoiding the problems associated with implants that are too large, too small, or of the wrong profile. Avoidance of breast implants that are too large not only reduces the risk of an unnatural appearance resulting from overfill, but equally importantly reduces the stress on the surrounding tissue and the risk of re-operation. On the other hand, avoiding underfill reduces the chance of "emptiness" in the upper breast, as well as a general lack of fullness. The ability to select between a combination of full and moderate height and full and moderate projection advantageously allows the doctor and patient to optimize the choice for women of differing heights and weights.

The body of both breast selector 100 and movable slides 101-103 are preferably constructed of cardboard or a similar rigid, lightweight material and the requisite information is printed in ink. In alternate embodiments, the body of breast selector 100 and/or slides 101-103 may be constructed of any one of a number of other materials, such as plastics or metals, and alternate techniques may be used for displaying the information, such as embossing or molding within the associated material.

An alternate embodiment of the principles of the present invention is shown in FIG. 2. Generally breast implant selector 200 is a tissue based optimal fill selector, which provides an optimal fill volume value based on breast width, skin stretch, parenchymal fill, and nipple-to-fold length. Table 19 provides representative information suitable for implementing the preferred embodiment of breast implant selector 200; the corresponding preferred algorithm is provided in Table 20. Generally, the patient's breast width provides the base measurement and an initial implant volume in cubic centimeters. The initial implant volume is then varied, up or down, in response to the measured skin stretch, fill, and nipple-to-fold determinations.

Breast implant selector system 200 is based on four (4) movable slides (selectors) 201-204 and four (4) corresponding windows 205-208. The construction and operation of breast implant selector 200 are similar to those of breast implant selector 100, although breast selector system 200 applies an algorithm based on four (4) input criteria. In the preferred embodiment of breast implant selector system 200, the input criteria are measured breast width, measured skin type (stretch), measured or observed breast tissue type, and nipple-to-fold length, with the corresponding result being an optimal implant fill.

Breast width slide 201 allows the doctor to input the patient's breast width by aligning the mark representing the measured value appearing within breast width window 205 with fixed arrow 209. In the illustrated embodiment, breast width slide 201 allows for the input of breast widths from narrow (Le. 10.5 cm) to very wide (i.e. 15.0 cm). When the appropriate breast width mark is aligned with arrow 209, movable arrow 210 on the edge of breast width slide 201 is set to a corresponding position within skin type window 206.

The patient's skin type is entered using skin type slide 202. In particular, the doctor aligns the corresponding skin type mark (arrow) (i.e. tight, average, loose, or very loose) on skin type slide 202 with movable arrow 210, as position by breast width slide 201. In turn, skin type slide 202 positions movable arrow 211 within breast tissue type window 207. The doctor then aligns the breast tissue type mark (arrow) on tissue type slide 203 with movable arrow 211, which in turn sets movable arrow 212 within fill (volume) window 208.

To determine the optimal fill, in centimeters squared (cc), the doctor aligns the appropriate nipple-to-fold arrow on fill slide 204 (i.e. normal or long) with arrow 212. The optimal fill (i.e. the fill that is the most natural and most proportionate) is then provided at fixed optimal fill arrow 213. The patient can request increased or decreased fill, although some trade-offs may be encountered. For example, with underfill, breast fullness and implant visibility decreases, while with overfill, the appearance becomes less natural, an upper bulge may occur, and the implant edges may become visible.

Figure 3:
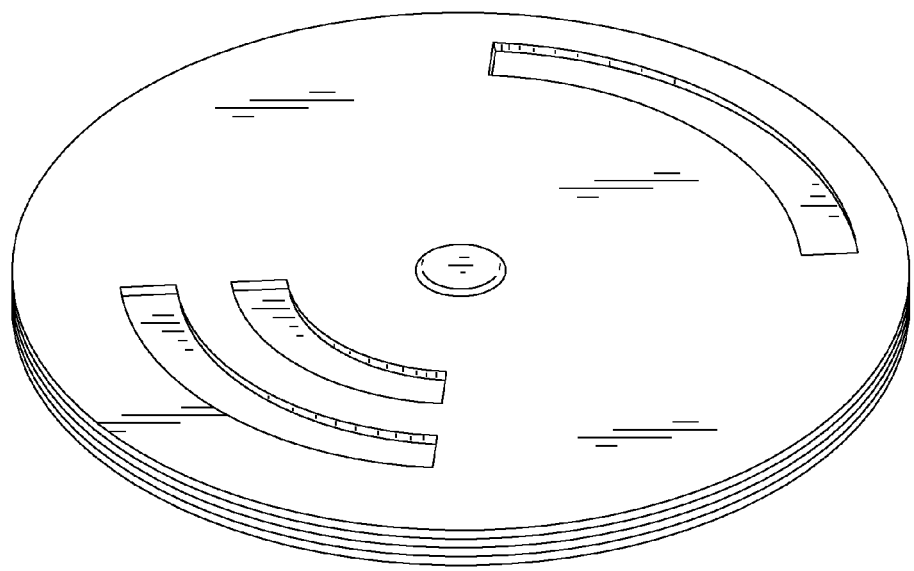
FIG. 3 is a simplified diagram of a circular slide rule embodying the principles of the present invention.

Is should be recognized that while the illustrated embodiments of breast implant selectors 100 and 200 are linear slide rules, in alternate embodiments of the present inventive principles, circular slide rules may also be used such as shown in FIG. 3. Furthermore, the information shown in the Tables, as well as the algorithms described above in conjunction with breast implant selectors 100 and 200, may also be utilized in electronic and software embodiments of these principles (e.g. hand-held electronic appliances and laptop computers).

Although the invention has been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiment disclosed might be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiments that fall within the true scope of the invention.

TABLE 1

BW 10.5

| | 10.5 Observation 1 | F Ht | M Ht | 10.5 Observation 2 | F HT | M Ht | 10.5 Observation 3 | F Ht | M Ht | 10.5ST |
|---|---|---|---|---|---|---|---|---|---|---|
| −60 | 140 | FM155 (9.5) | Augmentation Alone Not Recommended | 140 | Augmentation Alone Not Recommended | Augmentation Alone Not Recommended | 140 | | | 140 |
| −30 | 170 | 155FM | 160MM* | 170 | FM180 (10.0) | MM185 (10.5) | 170 | | | 170 |
| — | 200 | 205FM | 195MF | 200 | FM180 (10.0) | MM185 (10.5) | 200 | | | 200 |
| +30 | 230 | 220FF | 215MM | 230 | FF220 (10.5) | MF195 (10.5) | 230 | | | 230 |
| +60 | 260 | 220FF | 225MF | 260 | FF220 (10.5) | MX225 (10.5) | 260 | | | 260 |
| +90 | 290 | Augmentation Alone Not Recommended | Augmentation Alone Not Recommended | 290 | FX245 (10.5) | MX225 (10.5) | 290 | | | 290 |
| +120 | 320 | Augmentation Alone Not Recommended | Augmentation Alone Not Recommended | 320 | Augmentation Alone Not Recommended | Augmentation Alone Not Recommended | 320 | | | 320 |

| | F Ht | M Ht | Consensus Choices | | | | | lower | upper |
|---|---|---|---|---|---|---|---|---|---|
| −60 | FM155 (9.5) | MM160 (10.0) | FM155 (9.5) | MM160 (10.0) | FL 140 (10.0) | | | FM155 (9.5) | MM160 (10.0) |
| −30 | FM180 (10.0) | MM185 (10.5) | FM180 (10.0) | MM185 (10.5) | | | | FL140 (10.0) | MM185 (10.5) |
| — | FM205 (10.5) | MM185 (10.5) | FM205 (10.5) | MM185 (10.5) | 195MF | | | FM180 (10.0) | MF225 (11.0) |
| +30 | FF220 (10.5) | MF225 (11.0) | FF220 (10.5) | 215MM | MF225 (11.0) | MF195 (10.5) | | FM180 (10.0) | MF255 (11.5) |
| +60 | FF255 (11.0) | Augmentation Alone Not Recommended | 220FF | | FF255 (11.0) | | | FF220 (10.5) | FX280 (11.0) |
| +90 | Augmentation Alone Not Recommended | Augmentation Alone Not Recommended | Augmentation Alone Not Recommended | Augmentation Alone Not Recommended | | | | | |
| +120 | Augmentation Alone Not Recommended | Augmentation Alone Not Recommended | Augmentation Alone Not Recommended | Augmentation Alone Not Recommended | | | | | |

*preferred choice

TABLE 2

BW 11.0

| | Observation 1 | F Ht | M Ht | Observation 2 | F HT | M Ht | Observation 3 | F Ht | M Ht | 11ST |
|---|---|---|---|---|---|---|---|---|---|---|
| −60 | 190 | FL190 (11.0) | MM185 (10.5) | 190 | FM235 (11.0) | MM215 (11.0) | 190 | | | 190 |
| −30 | 220 | FM205 (10.5) | MM215 (11.0) | 220 | FM235 (11.0) | MM215 (11.0) | 220 | | | 220 |
| — | 250 | FM235 (11.0) | MF225 (11.0) | 250 | FF255 (11.0) | MF225 (11.0) | 250 | | | 250 |
| +30 | 280 | FM270 (11.5) | MF255 (11.5) | 280 | FF255 (11.0) | MF225 (11.0) | 280 | | | 280 |
| +60 | 310 | FF290 (11.5) | MF255 (11.5) | 310 | FX280 (11.0) | MX255 (11.0) | 310 | | | 310 |
| +90 | 340 | Augmentation Alone Not Recommended | Augmentation Alone Not Recommended | 340 | FX280 (11.0) | MX255 (11.0) | 340 | | | 340 |
| +120 | 370 | Augmentation Alone Not | Augmentation Alone Not | 370 | Augmentation Alone Not | Augmentation Alone Not | 370 | | | 370 |

TABLE 2-continued

BW 11.0

| | | Recommended | Recommended | | Recommended | Recommended | | |
|---|---|---|---|---|---|---|---|---|
| | F Ht | M Ht | | | | | | |
| −60 | FM205 (10.5) | MM185 (10.5) | FM205 (10.5) | MM185 (10.5) | MM215 (11.0) | FL190 (11.0) | MF225 (11.0) |
| −30 | FM235 (11.0) | MM215 (11.0) | FM205 (10.5) | FM235 (11.0) | MM215 (11.0) | FL190 (11.0) | MF225 (11.0) |
| — | FM235 (11.0) | MM245 (11.5) | FM235 (11.0) | MF225 (11.0) | FF255 (11.0) | FL220 (11.5) | MF255 (11.5) |
| +30 | FM270 (11.5) | MF255 (11.5) | FM270 (11.5) | MF255 (11.5) | FF255 (11.0) | FM235 (11.0) | MF255 (11.5) |
| +60 | FF290 (11.5) | Augmentation Alone Not Recommended | FF290 (11.5) | | | FM270 (11.5) | MX290 (11.5) |
| +90 | Augmentation Alone Not Recommended | Augmentation Alone Not Recommended | Augmentation Alone Not Recommended | Augmentation Alone Not Recommended | | | |
| +120 | Augmentation Alone Not Recommended | Augmentation Alone Not Recommended | Augmentation Alone Not Recommended | Augmentation Alone Not Recommended | | | |

*preferred choice

TABLE 3

BW 11.5

| | Observation 1 | F Ht | M Ht | Observation 2 | F HT | M Ht | Observation 3 | F Ht | M Ht | 11.5ST |
|---|---|---|---|---|---|---|---|---|---|---|
| −60 | 215 | FL220 (11.5) | MM215 (11.0) | 215 | FM235 (11.0) | MM245 (11.5) | 215 | | | 215 |
| −30 | 245 | FM235 (11.0) | MM245 (11.5) | 245 | FM235 (11.0) | MM245 (11.5) | 245 | | | 245 |
| — | 275 | FM270 (11.5) | MF255 (11.5) | 275 | FM270 (11.5) | MF255 (11.5) | 275 | | | 275 |
| +30 | 305 | FF290 (11.5) | MF295 (12.0) | 305 | FF290 (11.5) | MF255 (11.5) | 305 | | | 305 |
| +60 | 335 | FM310 (12.0) | MF295 (12.0) | 335 | FX315 (11.5) | MX290 (11.5) | 335 | | | 335 |
| +90 | 365 | Augmentation Alone Not Recommended | Augmentation Alone Not Recommended | 365 | FX315 (11.5) | MX290 (11.5) | 365 | | | 365 |
| +120 | 395 | Augmentation Alone Not Recommended | Augmentation Alone Not Recommended | 395 | FX315 (11.5) | Augmentation Alone Not Recommended | 395 | | | 395 |

| | F Ht | M Ht | | | | | | | |
|---|---|---|---|---|---|---|---|---|---|
| −60 | FF220 (10.5) | MM215 (11.0) | FL220 (11.5) | MM215 (11.0) | FM235 (11.0) | | | FL190 (11.0) | MF225 (11.0) |
| −30 | FM235 (11.0) | MM245 (11.5) | FM235 (11.0) | MM245 (11.5) | | | | FL220 (11.5) | MF255 (11.5) |
| — | FM270 (11.5) | MM245 (11.5) | FM270 (11.5) | MF255 (11.5) | | | | FM235 (11.0) | MX290 (11.5) |
| +30 | FF290 (11.5) | MM280 (12.0) | FF290 (11.5) | MF295 (12.0) | MM280 (12.0) | | | FM270 (11.5) | MX325 (12.0) |
| +60 | FM310 (12.0) | Augmentation Alone Not Recommended | FM310 (12.0) | MF295 (12.0) | | | 0.75 | FM310 (12.0) | MX325 (12.0) |
| +90 | Augmentation Alone Not Recommended | Augmentation Alone Not Recommended | Augmentation Alone Not Recommended | Augmentation Alone Not Recommended | | | | | |
| +120 | Augmentation Alone Not Recommended | Augmentation Alone Not Recommended | Augmentation Alone Not Recommended | Augmentation Alone Not Recommended | | | | | |

*preferred choice

TABLE 4

BW 12..0

| | Observation 1 | F Ht | M Ht | Observation 2 | F HT | M Ht | Observation 3 | F Ht | M Ht |
|---|---|---|---|---|---|---|---|---|---|
| −60 | 240 | FL250 (12.0) | MM245 (11.5) | 240 | FM270 (11.5) | MM280 (12.0) | 240 | | |
| −30 | 270 | FM270 (11.5) | MM280 (12.0) | 270 | FM270 (11.5) | MM280 (12.0) | 270 | | |
| — | 300 | FM310 (12.0) | MM280 (12.0) | 300 | FM310 (12.0) | MF295 (12.0) | 300 | | |
| +30 | 330 | FM310 (12.0) | MF295 (12.0) | 330 | FM310 (12.0) | MF295 (12.0) | 330 | | |
| +60 | 360 | FM350 (12.5) | MM320 (12.5) | 360 | FX360 (12.0) | MX325 (12.0) | 360 | | |
| +90 | 390 | Augmentation Alone Not Recommended | MF335 (12.5) | 390 | FX360 (12.0) | MX325 (12.0) | 390 | | |

TABLE 4-continued

| | | | | BW 12..0 | | | | |
|---|---|---|---|---|---|---|---|---|
| +120 | 420 | Augmentation Alone Not Recommended | Augmentation Alone Not Recommended | 420 | FX360 (12.0) | MX325 (12.0) | 420 | |

| | F Ht | M Ht | | | | | | |
|---|---|---|---|---|---|---|---|---|
| −60 | FM270 (11.5) | MM245 (11.5) | FM270 (11.5) | MM245 (11.5) | MM280 (12.0) | | FL220 (11.5) | MM280 (12.0) |
| −90 | FM270 (11.5) | MM280 (12.0) | FM270 (11.5) | MM280 (12.0) | | | FL250 (12.0) | MF295 (12.0) |
| — | FM310 (12.0) | MM280 (12.0) | FM310 (12.0) | MM280 (12.0) | MF295 (12.0) | | FM270 (11.5) | MX325 (12.0) |
| +30 | FM310 (12.0) | MF295 (12.0) | FM310 (12.0) | MF295 (12.0) | | | FM310 (12.0) | MF335 (12.5) |
| +60 | FM350 (12.5) | MF335 (12.5) | FM350 (12.5) | MM320 (12.5) | MF335 (12.5) | | FM350 (12.5) | MX370 (12.5) |
| +90 | FF375 (12.5) | Augmentation Alone Not Recommended | FF375 (12.5) | MF335 (12.5) | | | | |
| +120 | Augmentation Alone Not Recommended | Augmentation Alone Not Recommended | Augmentation Alone Not Recommended | Augmentation Alone Not Recommended | | | | |

*preferred choice

TABLE 5

| | | | | BW12.5 | | | | | | |
|---|---|---|---|---|---|---|---|---|---|---|
| | Observation 1 | F Ht | M Ht | Observation 2 | F HT | M Ht | Observation 3 | F Ht | M Ht | 12.5ST |
| −60 | 240 | FL220 (11.5) | MM245 (11.5) | 240 | FM310 (12.0) | MM280 (12.0) | 240 | | | 240 |
| −30 | 270 | FM270 (11.5) | MM280 (12.0) | 270 | FM310 (12.0) | MM280 (12.0) | 270 | | | 270 |
| — | 300 | FM310 (12.0) | MF295 (12.0) | 300 | FM350 (12.5) | MM320 (12.5) | 300 | | | 300 |
| +30 | 330 | FM310 (12.0) | MM320 (12.5) | 330 | FF375 (12.5) | MF335 (12.5) | 330 | | | 330 |
| +60 | 360 | FM350 (12.5) | MF335 (12.5) | 360 | FF375 (12.5) | MF335 (12.5) | 360 | | | 360 |
| +90 | 390 | Augmentation Alone Not Recommended | Augmentation Alone Not Recommended | 390 | FF375 (12.5) | MX370 (12.5) | 390 | | | 390 |
| +120 | 420 | Augmentation Alone Not Recommended | Augmentation Alone Not Recommended | 420 | FX410 (12.5) | MX370 (12.5) | 420 | | | 420 |

| | F Ht | M Ht | | | | | | |
|---|---|---|---|---|---|---|---|---|
| −60 | FM235 (11.0) | MM245 (11.5) | FM235 (11.0) | MM245 (11.5) | | | FL220 (11.5) | MF255 (11.5) |
| −30 | FM310 (12.0) | MM280 (12.0) | FM310 (12.0) | MM280 (12.0) | | | FL250 (12.0) | MF295 (12.0) |
| — | FM310 (12.0) | MM280 (12.0) | FM310 (12.0) | MM280 (12.0) | MM320 (12.5) | | FM270 (11.5) | MF335 (12.5) |
| +30 | FM350 (12.5) | MM320 (12.5) | FM350 (12.5) | MM320 (12.5) | FF375 (12.5) | MF335 (12.5) | FL320 (13.0) | MF375 (13.0) |
| +60 | FM350 (12.5) | MM360 (13.0) | FM350 (12.5) | MF335 (12.5) | MM360 (13.0) | FF375 (12.5) | FM310 (12.0) | MF375 (13.0) |
| +90 | FF375 (12.5) | MF375 (13.0) | FF375 (12.5) | MF375 (13.0) | | | | |
| +120 | Augmentation Alone Not Recommended | Augmentation Alone Not Recommended | Augmentation Alone Not Recommended | Augmentation Alone Not Recommended | | | | |

*preferred choice

TABLE 6

| | | | | BW13.0 | | | | | | |
|---|---|---|---|---|---|---|---|---|---|---|
| | Observation 1 | F Ht | M Ht | Observation 2 | F HT | M Ht | Observation 3 | F Ht | M Ht | 13ST |
| −60 | 265 | Augmentation Alone Not Recommended | ML220 (12.0) | 265 | FL320 (13.0) | ML285 (12.5) | 265 | | | 265 |
| −30 | 295 | FM310 (12.0) | MF295 (12.0) | 295 | FM350 (12.5) | MM320 (12.5) | 295 | | | 295 |
| — | 325 | FM310 (12.0) | MM320 (12.5) | 325 | FM350 (12.5) | MM360 (13.0) | 325 | | | 325 |
| +30 | 355 | FM310 (12.0) | MM360 (13.0) | 355 | FM395 (13.0) | MF375 (13.0) | 355 | | | 355 |
| +60 | 385 | FM395 (13.0) | MF375 (13.0) | 385 | FF425 (13.0) | MF375 (13.0) | 385 | | | 385 |
| +90 | 415 | Augmentation Alone Not Recommended | MM400 (13.5) | 415 | FF425 (13.0) | MX410 (13.0) | 415 | | | 415 |
| +120 | 445 | FX410 (12.5) | Augmentation Alone Not Recommended | 445 | | MX410 (13.0) | 445 | | | 445 |

TABLE 6-continued

BW13.0

|  | F Ht | M Ht |  |  |  |  |  |
|---|---|---|---|---|---|---|---|
| −60 | Augmentation Alone Not Recommended | MM280 (12.0) |  | ML285 (12.5) | MM280 (12.0) | FL250 (12.0) | MF295 (12.0) |
| −30 | FM310 (12.0) | MM280 (12.0) | FM310 (12.0) | MM280 (12.0) | MF295 (12.0) | MM280 (12.0) | MX325 (12.0) |
| — | FM350 (12.5) | MM320 (12.5) | FM350 (12.5) | MM320 (12.5) | MM360 (13.0) | FL320 (13.0) | MM360 (13.0) |
| +30 | FM350 (12.5) | MM360 (13.0) | FM350 (12.5) | MM360 (13.0) | MF375 (13.0) | FM350 (12.5) | MF375 (13.0) |
| +60 | FF375 (12.5) | MF375 (13.0) | MF375 (13.0) | MF375 (13.0) |  | FM350 (12.5) | MX410 (13.0) |
| +90 | Augmentation Alone Not Recommended | MF375 (13.0) | MF375 (13.0) | MF375 (13.0) |  |  |  |
| +120 | Augmentation Alone Not Recommended | Augmentation Alone Not Recommended | Augmentation Alone Not Recommended | Augmentation Alone Not Recommended |  |  |  |

*preferred choice

TABLE 7

BW13.5

|  | Observation 1 | F Ht | M Ht | Observation 2 | F HT | M Ht | Observation 3 | F Ht | M Ht | 13.5ST |
|---|---|---|---|---|---|---|---|---|---|---|
| −60 | 290 | Augmentation Alone Not Recommended | ML285 (12.5) | 290 | FL320 (13.0) | MM320 (12.5) | 290 |  |  | 290 |
| −30 | 320 | FL320 (13.0) | MM320 (12.5) | 320 | FM350 (12.5) | MM360 (13.0) | 320 |  |  | 320 |
| — | 350 | FM350 (12.5) | MM360 (13.0) | 350 | FM395 (13.0) | MM400 (13.5) | 350 |  |  | 350 |
| +30 | 380 | FF375 (12.5) | MF375 (13.0) | 380 | FM395 (13.0) | MF420 (13.5) | 380 |  |  | 380 |
| +60 | 410 | FM395 (13.0) | MM400 (13.5) | 410 | FF425 (13.0) | MF420 (13.5) | 410 |  |  | 410 |
| +90 | 440 | Augmentation Alone Not Recommended | MF420 (13.5) | 440 | FX410 (12.5) | MX445 (13.5) | 440 |  |  | 440 |
| +120 | 470 | FX410 (12.5) | Augmentation Alone Not Recommended | 470 |  | MX445 (13.5) | 470 |  |  | 470 |

|  | F Ht | M Ht |  |  |  |  |  |
|---|---|---|---|---|---|---|---|
| −60 | Augmentation Alone Not Recommended | Augmentation Alone Not Recommended |  | ML285 (12.5) | MM320 (12.5) |  | ML285 (12.5) | MM360 (13.0) |
| −30 | Augmentation Alone Not Recommended | MM360 (13.0) |  | MM320 (12.5) | MM360 (13.0) |  | MM320 (12.5) | MM360 (13.0) |
| — | FM350 (12.5) | MM360 (13.0) | FM350 (12.5) | MM360 (13.0) | FM395 (13.0) | MM400 (13.5) | FM310 (12.0) | MM400 (13.5) |
| +30 | FF375 (12.5) | MF375 (13.0) | FF375 (12.5) | FM395 (13.0) | MF375 (13.0) | MF420 (13.5) | FM350 (12.5) | MF420 (13.5) |
| +60 | FM395 (13.0) | MM400 (13.5) | FM395 (13.0) | MM400 (13.5) | FF425 (13.0) | MF420 (13.5) | FM395 (13.0) | MX410 (13.0) |
| +90 | Augmentation Alone Not Recommended | MF420 (13.5) | Augmentation Alone Not Recommended | MF420 (13.5) |  |  |  |  |
| +120 | Augmentation Alone Not Recommended | Augmentation Alone Not Recommended | Augmentation Alone Not Recommended | Augmentation Alone Not Recommended |  |  |  |  |

*preferred choice

TABLE 8

BW14.0

|  | Observation 1 | F Ht | M Ht | Observation 2 | F HT | M Ht | Observation 3 | F Ht | M Ht | 14ST |
|---|---|---|---|---|---|---|---|---|---|---|
| −60 | 315 | Augmentation Alone Not Recommended | MM320 (12.5) | 315 | FL320 (13.0) | MM360 (13.0) | 315 |  |  | 315 |
| −30 | 345 | FL320 (13.0) | MM360 (13.0) | 345 | FM395 (13.0) | MM360 (13.0) | 345 |  |  | 345 |
| — | 375 | FM395 (13.0) | MM400 (13.5) | 375 | FM395 (13.0) | MM360 (13.0) | 375 |  |  | 375 |
| +30 | 405 | FM395 (13.0) | MM400 (13.5) | 405 | FM440 (13.5) | MF420 (13.5) | 405 |  |  | 405 |
| +60 | 435 | Augmentation Alone Not Recommended | MM400 (13.5) | 435 |  | MF420 (13.5) | 435 |  |  | 435 |

TABLE 8-continued

BW14.0

| | | | | | | | |
|---|---|---|---|---|---|---|---|
| +90 | 465 | Augmentation Alone Not Recommended | Augmentation Alone Not Recommended | 465 | | 465 | 465 |
| +120 | 495 | Augmentation Alone Not Recommended | Augmentation Alone Not Recommended | 495 | | 495 | 495 |

| | F Ht | M Ht | | | | | |
|---|---|---|---|---|---|---|---|
| −60 | Augmentation Alone Not Recommended | Augmentation Alone Not Recommended | FL320 (13.0) | MM320 (12.5) | MM360 (13.0) | FL320 (13.0) | MM360 (13.0) |
| −30 | Augmentation Alone Not Recommended | MM360 (13.0) | MM360 (13.0) | MM360 (13.0) | | FL320 (13.0) | MF375 (13.0) |
| — | FM395 (13.0) | MM360 (13.0) | FM395 (13.0) | MM360 (13.0) | MM400 (13.5) | FL320 (13.0) | MF420 (13.5) |
| +30 | FM395 (13.0) | MM400 (13.5) | FM395 (13.0) | MM400 (13.5) | MF420 (13.5) | FM395 (13.0) | MF420 (13.5) |
| +60 | Augmentation Alone Not Recommended | MM400 (13.5) | | MM400 (13.5) | MF420 (13.5) | MM400 (13.5) | MX445 (13.5) |
| +90 | Augmentation Alone Not Recommended | Augmentation Alone Not Recommended | Augmentation Alone Not Recommended | Augmentation Alone Not Recommended | | | |
| +120 | Augmentation Alone Not Recommended | Augmentation Alone Not Recommended | Augmentation Alone Not Recommended | Augmentation Alone Not Recommended | | | |

*preferred choice

TABLE 9

ML170 (11.0)
ML195 (11.5)
ML220 (12.0)
ML285 (12.5)
MM160 (10.0)
MM185 (10.5)
MM215 (11.0)
MM245 (11.5)
MM280 (12.0)
MM320 (12.5)
MM360 (13.0)
MM400 (13.5)
MM450 (14.0)
MF165 (10.0)
MF195 (10.5)
MF225 (11.0)
MF255 (11.5)
MF295 (12.0)
MF335 (12.5)
MF375 (13.0)
MF420 (13.5)
MX165 (9.5)
MX195 (10.0)
MX225 (10.5)
MX255 (11.0)
MX290 (11.5)
MX325 (12.0)
MX370 (12.5)
MX410 (13.0)
MX445 (13.5)
FL140 (10.0)
FL190 (11.0)
FL220 (11.5)
FL250 (12.0)
FL320 (13.0)
FM155 (9.5)
FM180 (10.0)
FM205 (10.5)
FM235 (11.0)
FM270 (11.5)
FM310 (12.0)
FM350 (12.5)
FM395 (13.0)
FM440 (13.5)
FF160 (9.5)
FF185 (10.0)
FF220 (10.5)
FF255 (11.0)
FF290 (11.5)
FF375 (12.5)
FF425 (13.0)
FX185 (9.5)
FX215 (10.0)
FX245 (10.5)
FX280 (11.0)
FX315 (11.5)
FX360 (12.0)
FX410 (12.5)
Augmentation Alone Not Recommended
FF185 (10.0)

TABLE 10

BW10.5

| | | Observation 1 | Best Choice | Observation 2 | Best Choice | Observation 3 | Best Choice | ST | Best Choice | Consensus |
|---|---|---|---|---|---|---|---|---|---|---|
| SS | −60 | 140 | Style 10 150 (10.1) | 140 | | 140 | | 140 | Style 10 150 (10.1) | Style 10 150 (10.1) | Style 10 150 (10.1) |
| | −30 | 170 | Style 10 180 | 170 | | 170 | | 170 | Style 10 | Style 10 | Style 10 180 (10.7) |

TABLE 10-continued

BW10.5

| | | Observation 1 | Best Choice | Observation 2 | Best Choice | Observation 3 | Best Choice | ST | Best Choice | | | Consensus |
|---|---|---|---|---|---|---|---|---|---|---|---|---|
| | | | (10.7) | | | | | | 180 (10.7) | 180 (10.7) | | |
| | — | 200 | Style 15 194 (10.3) | 200 | | 200 | | 200 | Style 10 210 (11.2) | Style 15 194 (10.3) | | Style 10 210 (11.2) |
| | +30 | 230 | Style 15 234 (10.9) | 230 | | 230 | | 230 | Style 10 240 (11.7) | Style 15 234 (10.9) | | Style 10 240 (11.7) |
| | +60 | 260 | Style 20 260 (10.4) | 260 | | 260 | | 260 | Style 10 240 (11.7) | Style 20 260 (10.4) | Style 10 240 (11.7) | Style 10 270 (12.2) |
| | +90 | 290 | Style 20 280 (10.6) | 290 | | 290 | | 290 | Style 10 270 (12.2) | | | Style 10 300 (12.6) |
| | +120 | 320 | Augmentation Alone Not Recommended | 320 | | 320 | | 320 | Style 15 304 (11.9) | | | Style 10 330 (13.0) |
| | | | | | | | | | | | | Style 10 360 (13.4) |
| | | | | | | | | | | | | Style 10 390 (13.6) |
| | | | | | | | | | | | | Style 10 420 (14.0) |
| | | | | | | | | | | | | Style 10 450 (14.4) |

*preferred choice

TABLE 11

BW11.0

| | | | | | | | | | | | | |
|---|---|---|---|---|---|---|---|---|---|---|---|---|
| | | *preferred choice | | | | | | | | | | Style 15 158 (9.5) |
| | | Observation 1 | Best Choice | Observation 2 | Best Choice | Observation 3 | Best Choice | ST | Best Choice | | | Style 15 176 (9.9) |
| SS | −60 | 190 | Style 10 180 (10.7) | 190 | | 190 | | 190 | Style 10 180 (10.7) | Style 10 180 (10.7) | | Style 15 194 (10.3) |
| | −30 | 220 | Style 10 210 (11.2) | 220 | | 220 | | 220 | Style 10 210 (11.2) | Style 10 210 (11.2) | | Style 15 213 (10.6) |
| | — | 250 | Style 15 234 (10.9) | 250 | | 250 | | 250 | Style 10 240 (11.7) | Style 15 234 (10.9) | | Style 15 234 (10.9) |
| | +30 | 280 | Style 15 286 (11.7) | 280 | | 280 | | 280 | Style 10 270 (12.2) | Style 15 286 (11.7) | Style 10 270 (12.2) | Style 15 265 (11.4) |
| | +60 | 310 | Style 20 300 (10.9) | 310 | | 310 | | 310 | Style 10 300 (12.6) | Style 20 300 (10.9) | Style 10 300 (12.6) | Style 15 286 (11.7) |
| | +90 | 340 | Style 20 325 (11.2) | 340 | | 340 | | 340 | Style 10 330 (13.0) | | | Style 15 304 (11.9) |
| | +120 | 370 | Augmentation Alone Not Recommended | 370 | | 370 | | 370 | Style 15 339 (12.4) | | | Style 15 339 (12.4) |
| | | | | | | | | | | | | Style 15 371 (12.9) |
| | | | | | | | | | | | | Style 15 397 (13.1) |
| | | | | | | | | | | | | Style 15 421 (13.3) |
| | | | | | | | | | | | | Style 15 457 (13.7) |

TABLE 12

BW11.5

| | | | | | | | | | | | | |
|---|---|---|---|---|---|---|---|---|---|---|---|---|
| | | *preferred choice | | | | | | | | | | Style 20 140 (9.1) |
| | | Observation 1 | Best Choice | Observation 2 | Best Choice | Observation 3 | Best Choice | ST | Best Choice | | | Style 20 160 (9.4) |
| SS | −60 | 215 | Style 10 210 (11.2) | 215 | | 215 | | 215 | Style 10 210 (11.2) | Style 10 210 (11.2) | | Style 20 180 (9.6) |

TABLE 12-continued

| | | | | BW11.5 | | | | | | | |
|---|---|---|---|---|---|---|---|---|---|---|---|
| | −30 | 245 | Style 10 240 (11.7) | 245 | 245 | 245 | Style 10 240 (11.7) | Style 10 240 (11.7) | | Style 20 200 (9.7) |
| | — | 275 | Style 15 265 (11.4) | 275 | 275 | 275 | Style 10 270 (12.2) | Style 15 265 (11.4) | Style 10 270 (12.2) | Style 20 230 (10.0) |
| | +30 | 305 | Style 15 304 (11.9) | 305 | 305 | 305 | Style 10 300 (12.6) | Style 15 304 (11.9) | Style 10 300 (12.6) | Style 20 260 (10.4) |
| | +60 | 335 | Style 15 339 (12.4) | 335 | 335 | 335 | Style 10 330 (13.0) | Style 15 339 (12.4) | Style 10 330 (13.0) | Style 20 280 (10.6) |
| | +90 | 365 | Style 20 350 (11.4) | 365 | 365 | 365 | Style 10 360 (13.4) | | | Style 20 300 (10.9) |
| | +120 | 395 | Augmentation Alone Not Recommended | 395 | 395 | 395 | Style 15 397 (13.1) | | | Style 20 325 (11.2) |
| | | | | | | | | | | Style 20 350 (11.4) |
| | | | | | | | | | | Style 20 375 (11.7) |
| | | | | | | | | | | Style 20 400 (11.9) |

TABLE 13

| | | | | BW12.0 | | | | | | | |
|---|---|---|---|---|---|---|---|---|---|---|---|
| | | | *preferred choice | | | | | | | | Style 20 425 (12.0) |
| | | Observation 1 | Best Choice | Observation 2 | Best Choice | Observation 3 | Best Choice | ST | Best Choice | | Style 20 450 (12.4) |
| SS | −60 | 240 | Style 10 240 (11.7) | 240 | | 240 | | 240 | Style 10 240 (11.7) | Style 10 240 (11.7) | Augmentation Alone Not Recommended |
| | −30 | 270 | Style 10 270 (12.2) | 270 | | 270 | | 270 | Style 10 270 (12.2) | Style 10 270 (12.2) | |
| | — | 300 | Style 15 304 (11.9) | 300 | | 300 | | 300 | Style 10 300 (12.6) | Style 10 300 (12.6) | Style 15 304 (11.9) |
| | +30 | 330 | Style 15 339 (12.4) | 330 | | 330 | | 330 | Style 10 330 (13.0) | Style 10 330 (13.0) | Style 15 339 (12.4) |
| | +60 | 360 | Style 15 371 (12.9) | 360 | | 360 | | 360 | Style 10 360 (13.4) | Style 15 371 (12.9) | |
| | +90 | 390 | Style 20 400 (11.9) | 390 | | 390 | | 390 | Style 10 390 (13.6) | | |
| | +120 | 420 | Augmentation Alone Not Recommended | 420 | | 420 | | 420 | Style 15 421 (13.3) | | |

TABLE 14

| | | | | BW12.5 | | | | | |
|---|---|---|---|---|---|---|---|---|---|
| | | Observation 1 | Best Choice | Observation 2 | Best Choice | Observation 3 | Best Choice | ST | Best Choice | |
| SS | −60 | 240 | Style 10 240 (11.7) | 240 | | 240 | | 240 | Style 10 240 (11.7) | Style 10 240 (11.7) |
| | −30 | 270 | Style 10 270 (12.2) | 270 | | 270 | | 270 | Style 10 270 (12.2) | Style 10 270 (12.2) |
| | — | 300 | Style 10 300 (12.6) | 300 | | 300 | | 300 | Style 10 300 (12.6) | Style 10 300 (12.6) |
| | +30 | 330 | Style 10 330 (13.0) | 330 | | 330 | | 330 | Style 10 330 (13.0) | Style 10 330 (13.0) |

TABLE 14-continued

BW12.5

| | | Observation 1 | Best Choice | Observation 2 | Best Choice | Observation 3 | Best Choice | ST | Best Choice | | |
|---|---|---|---|---|---|---|---|---|---|---|---|
| | +60 | 360 | Style 15 371 (12.9) | 360 | | 360 | | 360 | Style 10 360 (13.4) | Style 10 360 (13.4) | Style 15 371 (12.9) |
| | +90 | 390 | Style 15 371 (12.9) | 390 | | 390 | | 390 | Style 10 390 (13.6) | | |
| | +120 | 420 | Augmentation Alone Not Recommended | 420 | | 420 | | 420 | Style 15 421 (13.3) | | |

*preferred choice

TABLE 15

BW13.0

| | | Observation 1 | Best Choice | Observation 2 | Best Choice | Observation 3 | Best Choice | ST | Best Choice | |
|---|---|---|---|---|---|---|---|---|---|---|
| SS | −60 | 265 | Style 10 270 (12.2) | 265 | | 265 | | 265 | Style 10 270 (12.2) | Style 10 270 (12.2) |
| | −30 | 295 | Style 10 300 (12.6) | 295 | | 295 | | 295 | Style 10 300 (12.6) | Style 10 300 (12.6) |
| | — | 325 | Style 10 330 (13.0) | 325 | | 325 | | 325 | Style 10 330 (13.0) | Style 10 330 (13.0) |
| | +30 | 355 | Style 10 360 (13.4) | 355 | | 355 | | 355 | Style 10 360 (13.4) | Style 10 360 (13.4) |
| | +60 | 385 | Style 10 390 (13.6) | 385 | | 385 | | 385 | Style 10 390 (13.6) | Style 10 390 (13.6) |
| | +90 | 415 | Style 10 420 (14.0) | 415 | | 415 | | 415 | Style 10 420 (14.0) | |
| | +120 | 445 | Augmentation Alone Not Recommended | 445 | | 445 | | 445 | Style 10 450 (14.4) | |

*preferred choice

TABLE 16

BW13.5

| | | Observation 1 | Best Choice | Observation 2 | Best Choice | Observation 3 | Best Choice | ST | Best Choice | |
|---|---|---|---|---|---|---|---|---|---|---|
| SS | −60 | 290 | Style 10 300 (12.6) | 290 | | 290 | | 290 | Style 10 300 (12.6) | Style 10 300 (12.6) |
| | −30 | 320 | Style 10 330 (13.0) | 320 | | 320 | | 320 | Style 10 330 (13.0) | Style 10 330 (13.0) |
| | — | 350 | Style 10 360 (13.4) | 350 | | 350 | | 350 | Style 10 360 (13.4) | Style 10 360 (13.4) |
| | +30 | 380 | Style 10 390 (13.6) | 380 | | 380 | | 380 | Style 10 390 (13.6) | Style 10 390 (13.6) |
| | +60 | 410 | Style 10 420 (14.0) | 410 | | 410 | | 410 | Style 10 420 (14.0) | Style 10 420 (14.0) |
| | +90 | 440 | Style 15 421 (13.3) | 440 | | 440 | | 440 | Style 10 450 (14.4) | |
| | +120 | 470 | Augmentation Alone Not Recommended | 470 | | 470 | | 470 | Augmentation Alone Not Recommended | |

*preferred choice

TABLE 17

BW14.0

|  |  | Observation 1 | Best Choice | Observation 2 | Best Choice | Observation 3 | Best Choice | ST | Best Choice | |
|---|---|---|---|---|---|---|---|---|---|---|
| SS | −60 | 315 | Style 10 330 (13.0) | 315 |  | 315 |  | 315 | Style 10 300 (12.6) | Style 10 300 (12.6) |
|  | −30 | 345 | Style 10 360 (13.4) | 345 |  | 345 |  | 345 | Style 10 330 (13.0) | Style 10 360 (13.4) |
|  | — | 375 | Style 10 360 (13.4) | 375 |  | 375 |  | 375 | Style 10 360 (13.4) | Style 10 360 (13.4) |
|  | +30 | 405 | Style 10 390 (13.6) | 405 |  | 405 |  | 405 | Style 10 390 (13.6) | Style 10 390 (13.6) |
|  | +60 | 435 | Style 10 420 (14.0) | 435 |  | 435 |  | 435 | Style 10 420 (14.0) | Style 10 420 (14.0) |
|  | +90 | 465 | Style 10 450 (14.4) | 465 |  | 465 |  | 465 | Style 10 450 (14.4) |  |
|  | +120 | 495 | Augmentation Alone Not Recommended | 495 |  | 495 |  | 495 | Augmentation Alone Not Recommended |  |

*preferred choice

TABLE 18

| Full Height/Moderate Projection FM | | | Full Height/Moderate Projection FF | | | Full Height/Moderate Projection MM | | | Full Height/Moderate Projection MF | | |
|---|---|---|---|---|---|---|---|---|---|---|---|
| Width | Height | Size | Width | Height | Size | Width | Height | Size | Width | Height | Size |
| 10.0 cm | 10.5 | 180 | 10.0 | 10.5 | 185 | 10.0 | 9.1 | 160 | 10.0 | 9.1 | 165 |
| 10.5 cm | 11.0 | 205 | 10.5 | 11.0 | 220 | 10.5 | 9.6 | 185 | 10.5 | 9.6 | 195 |
| 11.0 cm | 11.5 | 235 | 11.0 | 11.5 | 255 | 11.0 | 10.1 | 215 | 11.0 | 10.1 | 225 |
| 11.5 cm | 12.0 | 270 | 11.5 | 12.0 | 290 | 11.5 | 10.6 | 245 | 11.5 | 10.6 | 255 |
| 12.0 cm | 12.5 | 310 |  |  |  | 12.0 | 11.1 | 280 | 12.0 | 11.1 | 295 |
| 12.5 cm | 13.0 | 350 | 12.5 | 13.0 | 375 | 12.5 | 11.6 | 320 | 12.5 | 11.6 | 335 |
| 13.0 cm | 13.5 | 395 | 13.0 | 13.5 | 425 | 13.0 | 12.1 | 360 | 13.0 | 12.1 | 375 |
| 13.5 cm | 14.0 | 440 | 13.5 | 14.0 | 475 | 13.5 | 12.5 | 400 | 13.5 | 12.5 | 420 |
| 14.0 cm | 14.5 | 500 | 14.0 | 14.5 | 535 | 14.0 | 12.9 | 450 | 14.0 | 12.9 | 470 |

TABLE 19

BREAST IMPLANT CHART - RANGE OF POSSIBILITIES
SHADED ROW INDICATES "STARTING VOLUME" DETERMINED
BY BASE WIDTH (NUMBERS ALONG THE TOP) ONE THEN ADDS OR
SUBTRACTS ACCORDING TO THE SKIN STRETCH, FILL, AND
NIPPLE FOLD MEASUREMENTS, AS SHOWN IN TABLE 20.

|  | 10.5 | 11 | 11.5 | 12 | 12.5 | 13 | 13.5 | 14 | 14.5 | 15 |
|---|---|---|---|---|---|---|---|---|---|---|
| −60 | 140 | 190 | 215 | 240 | 240 | 265 | 290 | 315 | 315 | 340 |
| −30 | 170 | 220 | 245 | 270 | 270 | 295 | 320 | 345 | 345 | 370 |
| — | 200 | 250 | 275 | 300 | 300 | 325 | 350 | 375 | 375 | 400 |
| +30 | 230 | 280 | 305 | 330 | 330 | 355 | 380 | 405 | 405 | 430 |
| +60 | 260 | 310 | 335 | 360 | 360 | 385 | 410 | 435 | 435 | 460 |
| +90 | 290 | 340 | 365 | 390 | 390 | 415 | 440 | 465 | 465 | 490 |
| +120 | 320 | 370 | 395 | 420 | 420 | 445 | 470 | 495 | 495 | 520 |

TABLE 20

Determining Optimum Implant Volume

STEP 1
Width

| B.W. Parenchyma (cm) | 10.5 | 11.0 | 11.5 | 12.0 | 12.5 | 13.0 | 13.5 | 14.0 | 14.5 | 15.0 |
|---|---|---|---|---|---|---|---|---|---|---|
| Initial Volume (cc) | 200 | 250 | 275 | 300 | 300 | 325 | 350 | 375 | 375 | 400 |
|  | Narrow | | | Average | | | Wide | | Very Wide | |

STEP 2
Skin Stretch

| <2 cm −30 cc | 2-3 cm (no change) | 3-4 cm +30 cc | >4 cm +60 |
|---|---|---|---|
| Tight | Average | Loose | Very Loose |

TABLE 20-continued

STEP 3
Fill

| <20% full +30 | 20-80% (no change) | >80% −30 cc |
|---|---|---|
| Empty | Average | Full |

STEP 4
Nipple-Fold (on maximal stretch)

| <9 cm (no adjustment) | >9.5 +30 cc |
|---|---|
| Normal | Long |

CONCLUSION
Wheel/Chart should now show optimum implant volume
Final Volume should also show a N: IMF distance as follows:

| 200 | 250 | 275 | 300 | 325 | 350 | 375 | 400 |
|---|---|---|---|---|---|---|---|
| 7.0 | 7.0 | 7.5 | 8 | 8 | 8.5 | 9.0 | 9.5 |

What is claimed is:

1. A breast implant selector system comprising:
    a breast width selector;
    a breast tissue type selector; and
    a result indicator providing a selected breast implant;
    the breast implant selector system being in the form of a circular slide rule.

2. The breast implant selector system of claim 1, further comprising a breast implant size selector.

3. The breast implant selector system of claim 2, wherein the breast selector system comprises a body having a plurality of windows and wherein:
    the breast implant selector comprises a first mechanical slide supported by the body for aligning breast width input information appearing in a first one of the windows with a first pointer;
    the breast tissue type selector comprises a second mechanical slide supported by the body for aligning breast tissue type input information appearing in a second one of the windows with a second pointer positioned within the second window by the first mechanical slide; and
    the implant size selector comprises a third mechanical slide supported by the body for aligning implant size input information appearing within a third one of the windows with a third pointer positioned within the third window by the second mechanical slide.

4. The breast implant selector system of claim 2, wherein:
    the breast width selector positions the selected breast width input information in a first window on the breast input selector;
    the breast tissue type selector positions the breast tissue type input information in a second window on the breast implant selector relative to a first pointer controlled by the breast width selector; and
    the implant size selector positions the implant size input information within a third window on the breast implant selector relative to a second pointer controlled by the breast tissue type selector.

5. The breast implant selector system of claim 4, wherein:
    the breast width selector comprises a first mechanical slide having a surface bearing selected breast width information and is movable relative to the first window such that at least some of the selected breast width information is visible through the first window;
    the breast tissue type selector comprises a second mechanical slide having a surface bearing selected breast tissue type information and is movable relative to the second window such that at least some of the selected breast tissue type information is visible through the second window; and
    the implant size selector comprises a third mechanical slide having a surface bearing selected implant size information and is movable relative to the third window such that at least some of the selected implant size information is visible through the third window.

6. The breast implant selector system of claim 5, wherein:
    the surface of the first mechanical slide further bears the first pointer and the first mechanical slide positions the first pointer within the second window; and
    the surface of the second mechanical slide further bears the second pointer and the second mechanical slide positions the second pointer within the third window.

7. The breast implant selector system of claim 6, wherein the result indicator comprises an result window and the surface of the third mechanical slide further bears the result and positions the result within the result window.

8. The breast implant selector system of claim 2, wherein the result includes a commercial breast implant designator.

9. The breast implant selector system of claim 8, wherein the result further includes a nipple-to-fold length value.

10. The breast implant selector system of claim 2, wherein the result includes breast implant fill information.

* * * * *

UNITED STATES PATENT AND TRADEMARK OFFICE
CERTIFICATE OF CORRECTION

PATENT NO. : 8,381,410 B2  
APPLICATION NO. : 13/155619  
DATED : February 26, 2013  
INVENTOR(S) : William P. Adams, Jr. et al.

Page 1 of 1

It is certified that error appears in the above-identified patent and that said Letters Patent is hereby corrected as shown below:

In the Specification

In column 4, line 57, delete "(Le." and insert -- (i.e. --, therefor.

In column 5, line 13, delete "Is" and insert -- It --, therefor.

In column 7-8, in Table 4, line 1, delete "BW 12..0" and insert -- BW 12.0 --, therefor.

Signed and Sealed this  
Thirtieth Day of September, 2014

Michelle K. Lee  
*Deputy Director of the United States Patent and Trademark Office*